(12) United States Patent
Ramesh et al.

(10) Patent No.: US 10,544,343 B2
(45) Date of Patent: Jan. 28, 2020

(54) VISCOMETER AND METHODS OF USE THEREOF

(71) Applicant: Schlumberger Technology Corporation, Sugar Land, TX (US)

(72) Inventors: Avinash Ramesh, Houston, TX (US); Garud Bindiganavale Sridhar, Sugar Land, TX (US); Jonathan Wun Shiung Chong, Sugar Land, TX (US); Rajesh Luharuka, Katy, TX (US); Lewis Callaway, Sugar Land, TX (US); Gregoire Omont, Houston, TX (US); Ivan Alaniz, McAllen, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 15/308,255

(22) PCT Filed: May 4, 2015

(86) PCT No.: PCT/US2015/029071
§ 371 (c)(1),
(2) Date: Nov. 1, 2016

(87) PCT Pub. No.: WO2015/168689
PCT Pub. Date: Nov. 5, 2015

(65) Prior Publication Data
US 2017/0058177 A1 Mar. 2, 2017

Related U.S. Application Data

(60) Provisional application No. 61/987,602, filed on May 2, 2014, provisional application No. 61/987,614, filed (Continued)

(51) Int. Cl.
*C09K 8/02* (2006.01)
*E21B 21/06* (2006.01)
(Continued)

(52) U.S. Cl.
CPC .............. *C09K 8/02* (2013.01); *C09K 8/42* (2013.01); *C09K 8/62* (2013.01); *E21B 21/062* (2013.01);
(Continued)

(58) Field of Classification Search
CPC ........ E21B 43/26; E21B 43/267; E21B 21/08; E21B 21/062; E21B 49/003; G01N 11/04;
(Continued)

(56) References Cited

U.S. PATENT DOCUMENTS 3,885,429 A 5/1975 Megyeri et al.
4,821,564 A 4/1989 Pearson et al.
(Continued)

FOREIGN PATENT DOCUMENTS

CN 1185476 C 1/2005
CN 103725265 A 4/2014
(Continued)

OTHER PUBLICATIONS

International Search Report issued in PCT/US2015/029071 dated Aug. 28, 2015; 3 pages.
(Continued)

*Primary Examiner* — Randy W Gibson
*Assistant Examiner* — Gedeon M Kidanu

(57) ABSTRACT

Disclosed herein is a method for viscosity measurement of non-Newtonian fluid for in-line measurement and process control. The process involves mixing additives to a base fluid to form the non-Newtonian fluid. The non-Newtonian fluid is fed to an in-line viscosity measurement device to obtain a rheological measurement. The addition of the additives to the base fluid is then adjusted based on the rheological measurement. A system for accomplishing the same is also disclosed.

20 Claims, 8 Drawing Sheets

Related U.S. Application Data on May 2, 2014, provisional application No. 62/019,589, filed on Jul. 1, 2014, provisional application No. 62/019,579, filed on Jul. 1, 2014.

(51) Int. Cl.
| | |
|---|---|
| *C09K 8/42* | (2006.01) |
| *C09K 8/62* | (2006.01) |
| *E21B 41/00* | (2006.01) |
| *G01N 11/02* | (2006.01) |
| *E21B 33/13* | (2006.01) |
| *E21B 43/26* | (2006.01) |

(52) U.S. Cl.
CPC .............. *E21B 41/00* (2013.01); *G01N 11/02* (2013.01); *E21B 33/13* (2013.01); *E21B 43/26* (2013.01)

(58) Field of Classification Search
CPC ....... G01N 2011/0026; G01N 30/6052; G01N 30/74; G01N 30/80; G01N 2030/027; G01N 11/00; B01D 15/24; F16L 11/127; B01F 2215/0081; B01F 3/1221; B01F 15/00246; B01F 5/102; B01F 15/00389
See application file for complete search history.

(56) References Cited

U.S. PATENT DOCUMENTS

| | | | | |
|---|---|---|---|---|
| 6,412,337 | B1 * | 7/2002 | Arzate .................. | G01N 11/08 73/54.02 |
| 8,372,789 | B2 | 2/2013 | Harris et al. | |
| 9,182,376 | B2 * | 11/2015 | Klasner ................. | G01N 29/022 |
| 2008/0127718 | A1 * | 6/2008 | Lesieur ................. | G01N 11/08 73/54.09 |
| 2009/0090504 | A1 * | 4/2009 | Weightman ............ | E21B 43/26 166/250.01 |
| 2009/0277638 | A1 | 11/2009 | Case et al. | |
| 2009/0277641 | A1 | 11/2009 | Walters et al. | |
| 2010/0044049 | A1 * | 2/2010 | Leshchyshyn ........... | C09K 8/68 166/308.1 |
| 2014/0053637 | A1 * | 2/2014 | Quillien ............... | G01N 1/2035 73/54.01 |
| 2014/0060175 | A1 | 3/2014 | Hutchings et al. | |
| 2015/0129210 | A1 * | 5/2015 | Chong ................... | E21B 33/13 166/280.1 |

FOREIGN PATENT DOCUMENTS

| | | |
|---|---|---|
| WO | 2012097424 A1 | 7/2012 |
| WO | 2014031639 A1 | 2/2014 |

OTHER PUBLICATIONS

Written Opinion issued in PCT/US2015/029071 dated Aug. 28, 2015; 11 pages.
Examination report issued in European Patent Appl. No. 15785501.6 dated Jul. 24, 2018; 4 pages.
Extended European Search Report issued in European Patent Appl. No. 15785501.6 dated Nov. 7, 2017; 8 pages.
Search Report issued in Russian Patent Appl. No. 2016147070 dated Sep. 7, 2017; 5 pages.
Decision on Grant issued in Russial Patent Application No. 2016147070 dated Jan. 9, 2018; 14 pages.

* cited by examiner

VISCOMETER AND METHODS OF USE THEREOF

This application is a 371 National Phase of International Patent Application PCT/US2015/029071 filed on May 4, 2015, which claims priority to Provisional Application No. 61/987,602 filed on May 2, 2014, Provisional Application No. 61/987,614 filed on May 2, 2016, Provisional Application No. 62/019,589 filed on Jul. 1, 2014, and Provisional Application No. 62/019,579 filed on Jul. 1, 2014. The entirety of each of these applications are incorporated herein by reference in their entirety.

BACKGROUND

Hydrocarbons (oil, natural gas, etc.) are obtained from a subterranean geologic formation (i.e., a "reservoir") by drilling a well that penetrates the hydrocarbon-bearing formation. The well provides a partial flowpath for the hydrocarbon to reach the surface. Production of the hydrocarbons (travel of the hydrocarbons from the formation to the wellbore and ultimately to the surface) occurs when a sufficiently unimpeded flowpath from the formation to the wellbore is present.

Hydraulic fracturing, also referred to as fracking, is a primary tool for improving well productivity by creating or extending fractures or channels from the wellbore to the reservoir. Pumping of propping granules, or proppants, during the hydraulic fracturing of oil and gas containing earth formations may enhance the hydrocarbon production capabilities of the earth formation. Hydraulic fracturing injects a viscous fluid into an oil and gas bearing earth formation under high pressure, which results in the creation or growth of fractures within the earth formation. These fractures serve as conduits for the flow of hydrocarbons trapped within the formation to the wellbore. To keep the fractures open and capable of supporting the flow of hydrocarbons to the wellbore, proppants are delivered to the fractures within the formation by a carrier fluid and fill the fracture with a proppant pack that is strong enough to resist closure of the fracture due to formation pressure and is also permeable for the flow of the fluids within the formation.

Most fracturing fluids contain a hydrophilic polymer dissolved in a solvent, such as water. The water-soluble polymers most often used are polysaccharides, guar and guar derivatives. A high level of viscosity of a hydrophilic polymer is reached when the polymer is properly hydrated.

In general, the hydration of a polymer is performed in hydration tanks with large volumes that accept a polymer phase gel and water mixture so as to produce a hydrated fluid as part of a continuous preparation of fracturing fluids. Such hydration tanks have focused primarily on mechanical mechanism movement or paddle based mixing processes which involve moving parts, as well as horse power to produce shear forces that increase the hydration rate of the hydratable polymer and establish the desired hydrated fluid viscosity at the hydration tank output. Various methods have been proposed to reduce the size of the hydration tank to increase the hydration rate of a gel during its residence time within the hydration tank.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to one or more embodiments disclosed herein is a method for viscosity measurement of non-Newtonian fluid for in-line measurement and process control including, adding additives to a base fluid to form the non-Newtonian fluid, feeding the non-Newtonian fluid to an in-line viscosity measurement device, measuring the viscosity of the non-Newtonian fluid to obtain a rheological measurement, and adjusting the addition of the additives to the base fluid based on the rheological measurement.

According to other embodiments disclosed herein is a system useful for preparing a slurry, the system including an additive and a base fluid, a base fluid supply, an additive supply feeder, a mixer that blends additive and base fluid to form a slurry, an in-line viscosity measurement device for measuring the viscosity of the slurry, a control system for adjusting the rate of the additive addition, and a pump for pumping the slurry to downstream systems.

Other aspects and advantages of the claimed subject matter will be apparent from the following description and the appended claims.

DETAILED DESCRIPTION

Figure 1:
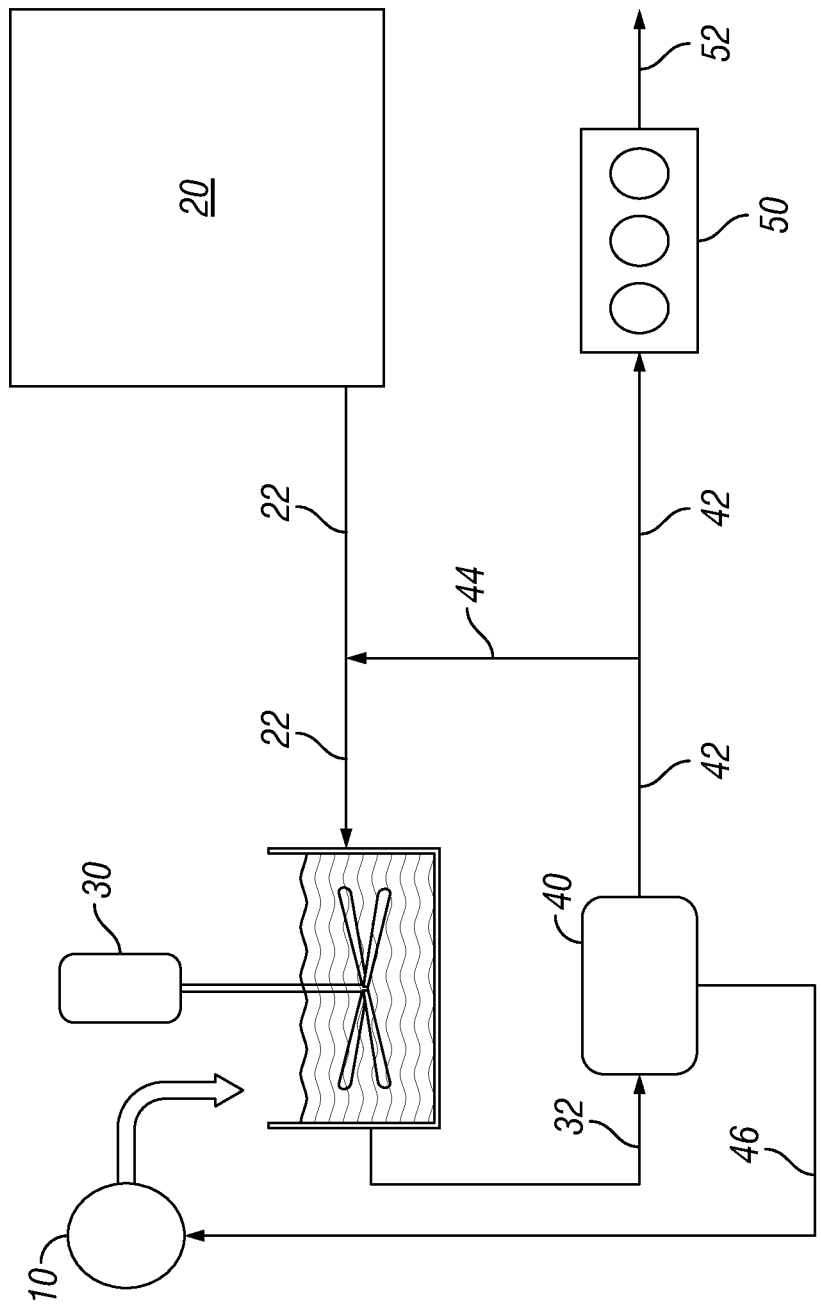
FIG. 1 illustrates a simplified process diagram according to one or more embodiments disclosed herein.

Reference will now be made in detail to embodiments of the present disclosure, examples of which are illustrated in the accompanying drawings. In the drawings and the following description, like reference numerals are used to designate like elements, where convenient. It will be appreciated that the following description is not intended to exhaustively show all examples, but is merely exemplary.

Generally, embodiments disclosed herein relate to methods in-line measurement and control of rheological properties of a fluid, particularly non-Newtonian fluids. More specifically, embodiments disclosed herein relate to the in-line measurement of a fracturing slurry viscosity, as well as methods of controlling the process in a manner to effect the viscosity of the slurry in real-time. Thus, in one or more embodiments, the control system may control a gel formation for the slurry based on viscosity measurements of the slurry exiting the system as a wellbore fracturing slurry being pumped downhole.

According to one or more embodiments disclosed herein, the present process relates to the use of in-line viscometer to provide feedback in such a manner as to enable process control of a treatment fluid. Viscosity is not conventionally measured in an in-line fashion in the oilfield services industry. Disclosed herein is a process for various techniques for in-line, real time, automated process control in the oilfield service industry using an in-line viscosity measurement of the treatment fluid.

Treatment fluids, according to one or more embodiments disclosed herein, may be used in a variety of subterranean treatments, including, but not limited to, stimulation treatments, drilling, and sand control treatments. As used herein, the term "treatment," or "treating," refers to any subterranean operation that uses a fluid in conjunction with a desired function and/or for a desired purpose. The term "treatment," or "treating," does not imply any particular action by the fluid or any particular component thereof. Examples of treatment fluids include cement or spacers for cementing applications, mud for drilling applications or guar-based gel for hydraulic fracturing applications. More specifically, the treatment fluid may be cement slurry comprised of water, cement (Class G, Class A, etc.), a dispersant, anti-foaming agent, retarding agent and an anti-settling agent. The spacer fluid system may be used to remove mud from a well or otherwise separate two types of fluids being circulated through the well and may include, for example, a hydrating polymer as well as a weighting agent for the desired density to be achieved. Regarding fracturing fluids, the fluid may be a guar-based gels, polyacrylamide-based gels, borate cross-linked gels and/or carboxymethylcellulose (CMC) based fluid systems. The drilling fluid may be water-based or oil-based (including invert emulsions) and may contain, for example, gelling agents, weighting agents (such as barite), etc.—In each of these fluid systems, the fluids are generally mixed at a wellsite prior to being pumped downhole. For example, referring to FIGS. 3 and 4, a fracturing site and a drill site, respectively, are shown and discussed below. At each of these sites, additives (liquids, solids, or gases) are generally mixed into a base fluid, but may also include formation of a concentrated solution at or remote from the site that is subsequently diluted at the site prior to being pumped downhole.

Each of the above-described fluids may be characterized as non-Newtonian. That is, while the viscosity of Newtonian fluid will remain constant regardless of the stress placed on it, the viscosity of a non-Newtonian fluid is dependent on the shear rate and can also be time dependent. Among above described treatment fluids, some of the classes of non-Newtonian fluids that may be used in accordance with the present disclosure include thixotropic fluids (such as xanthan containing fluids) and shear thinning fluids (such as fracturing fluids), while several models (Bingham Plastic, Power Law, Yield Power Law) have been developed to describe the rheology of various drilling fluids. The shear rate dependence of these non-Newtonian fluids has made in-line measurement of their viscosity challenging heretodate.

As described above, the in-line viscosity measurement for process control is desired to be used in fracturing, cementing and drilling. Currently, no viable process for in-line viscometery exists. In cementing and drilling, density and rheology are two important characteristics of the fluid that is being pumped into the well. However, there are cases where density of the fluid is difficult to measure, including low density cement slurries (particles at less than 2 $g/cm^3$), foamed cement systems, and fiber-laden cement systems. In such cases, the rheology of the fluid can be used to control the mixing process. Most of these fluids can be approximated to a Bingham-plastic fluid which is characterized by a yield point and plastic viscosity. The plastic viscosity can be measured using the in-line viscometer immediately downstream of the mixing device and the measurement can be used to control the mixing process to achieve a target viscosity. With a combination of density, which may or may not be measured by the inline viscometer, and rheology, specifically the viscosity, a process may be accurately controlled by the mixing of mud, cement or spacer in real time.

The process may be controlled in a number of ways. For example, by selecting a target viscosity, which may vary depending on the type of fluid being used, the metering of additives to the mixing system, that may be of different forms (liquid, solids, gas), can be adjusted in real-time through a high-speed feedback control loop. Target viscosities may be within a range of, for example, 1-10,000 cP. Alternatively, by monitoring viscosity, a measure of how well the fluid is mixed can be obtained and corrective steps to adjust mixing energy may be performed, such as increasing or decreasing mixer speed. In this case, density measurement alone may be inadequate. Additionally, by monitoring viscosity, events such as undesirable variations in dry blends ratios, or out-of-specification base fluids such as low pH levels, may be detected and trigger necessary actions such as alarms or shut-down sequences.

Further, process control based on density, alone, as feedback may not be able to detect the presence of finely entrained air/gas in the slurry. Because the metering of dry content is based on a target density, in the presence of finely entrained gas, more dry content will need to be added to compensate for the lack of density from the entrained air, effectively masking the presence of unwanted gas. In such a scenario, viscosity increases with the presence of finely entrained bubbles, which may trigger necessary process actions such as adding or increasing additives, or using mechanical means to remove the entrained air. As described above, viscosity is the preferred obtained measurement for rheological characterization of a fluid.

Referring now to the figures, shown in FIG. 1 is a simplified process diagram. An additive supply feeder 10 feeds an additive (which may optionally be a concentrated solution or solid) to mixer 30 where the additive is mixed with a base fluid (water, oil, etc.) fed through flow line 22 from fluid source 20. The additive is mixed with base fluid to form a mixed fluid 32, which may be a non-Newtonian fluid. Depending on the type of application, mixed fluid may be a drilling fluid, a cementing fluid, a spacer fluid, a fracturing slurry, etc. In various embodiments, mixed fluid 32 may be shear thinning, but other types of non-Newtonian fluids are envisioned as well. Mixed fluid 32 may then be fed to an in-line viscosity measurement device 40. The viscosity of the non-Newtonian fluid may be measured to obtain a rheological measurement and produce a measured effluent 42. The amount of additive being fed from feeder 10 to mixer 30 may be adjusted based on the rheological measurement through process control line 46.

Figure 2:
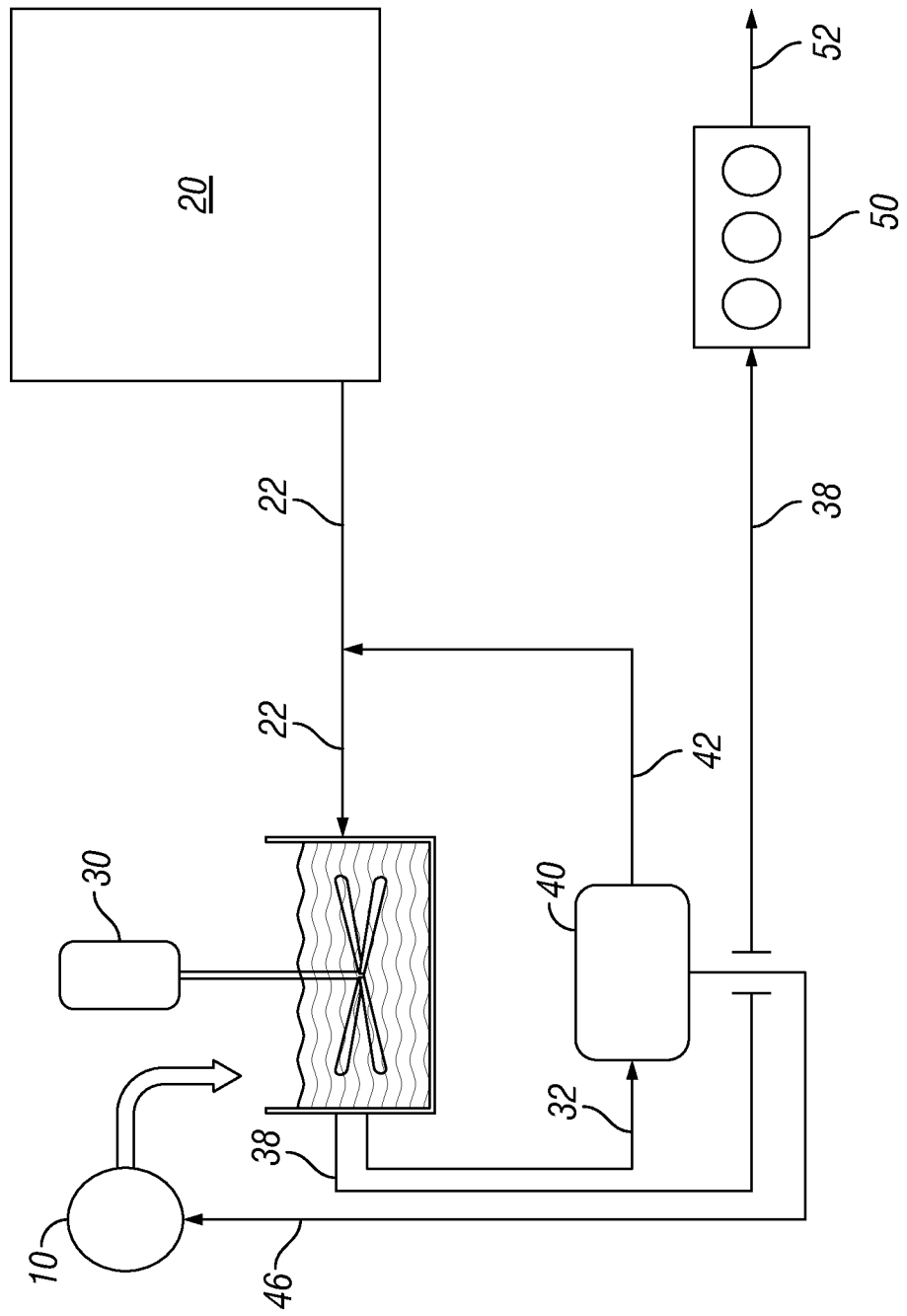
FIG. 2 illustrates a simplified process diagram according to one or more embodiments disclosed herein.

In general, the in-line viscometer should be placed as close to the mixer as possible for proper process control. This placement may avoid line losses and latency issues. Furthermore, regarding the in-line viscometer measurement device, a positive displacement pump may be coupled upstream with the instrument to maintain flow rate across the measuring device. In general, flow rate will correspond with the shear rate of the fluid. The pressure drop from the pump discharge to the end of the sampling line may also be affected by the conditions at the end of the line, and consequentially the measured viscosity may be skewed. For example, if the in-line viscosity measurement device is between the mixer and a downstream pump, the flow rates might vary, affecting the boundary conditions of the viscosity measurement. In such a case it may be required for the positive displacement pump feeding the viscosity measurement device to draw a separate sample from the mixer as opposed to the process flow loop and then recycle the sample back into the mixer. Such a case is illustrated in FIG. 2. As illustrated, mixed fluid 32 is fed to in-line viscosity measurement device 40 and measure effluent 42 is recycled back to mixer 30. This recycle loop may be open to the atmosphere to ensure the resistance to flow will purely be the shear against the pipe walls. Additionally, a second mixed fluid 38 bypasses in-line viscosity measurement device 40 and is fed directly to pump 50 and fed downhole, or to other downstream systems, via flow line 52.

Referring again to FIG. 1, a portion of measured effluent 42 may be fed to pump 50 and fed downhole, or to other downstream systems, via flow line 52. Additionally, a second portion of measured effluent 42 may be recycled via flow line 44 to fluid flow line 22 where it is fed back into mixer 30 for recycle and dilution. The fluid in being fed from fluid source 20 may be a pre-selected rate. The rate would be selected to meet the required volume needed for downhole operations, or for other downstream systems. Such a flow rate may also be based on the need and ability to recover fluid pumped downhole, such as the recovery of drilling fluids. Additionally, the flow rate may be selected such that the wellbore pressure is maintained. For example, the flow rate of fluid fed from fluid source 20 may be in the range of 0.01-120 bpm for fracturing fluids or for drilling fluids.

The viscosity of the mixed fluid 32 may correspond to a non-Newtown fluid and be in the range of between 1-10,000 cP at shear rates of 150-600 $s^{-1}$. To maintain this viscosity, the in-line viscosity measurement device 40 may send a signal via process control line 46 to additive feeder 10. In response to this signal, the feed rate of the additive may be adjusted by either an increase or decrease in the amount of additive being fed to mixer 30. For example, the concentration solution may be fed at a rate in the range of between 0.001-50 bpm.

In various embodiments, the control system (not shown) that has the ability to control the viscosity of the fluid to an optimum value based on the desired job specifics (downhole slurry rate and concentration for a fracturing slurry, for example) is used. Specifically, the control system is configured to supply a certain amount of additive into the mixer with base fluid, and to dilute the additive with the base fluid to obtain the predefined slurry viscosity. Various elements throughout the process such as the amount of the additive added to produce the slurry, the residence time in the mixer or hydration tank (when a hydratable polymer is present as one of the additives), and the dilution process in the mixer may affect the final fluid viscosity. Therefore, these elements may be carefully controlled to specific optimum values.

Figure 3:
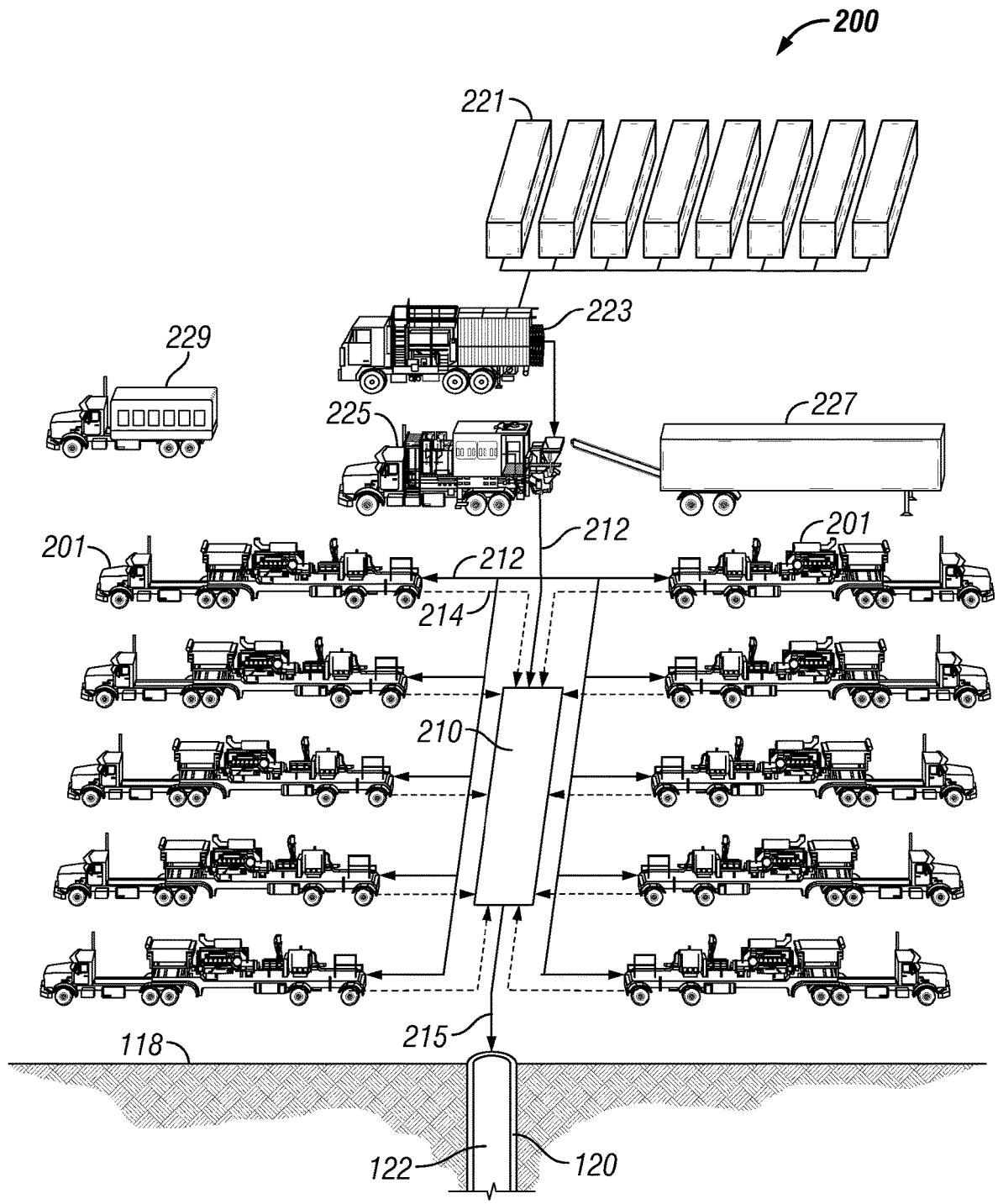
FIG. 3 illustrates a simplified process diagram of a fracturing site according to one or more embodiments disclosed herein.
Figure 4:
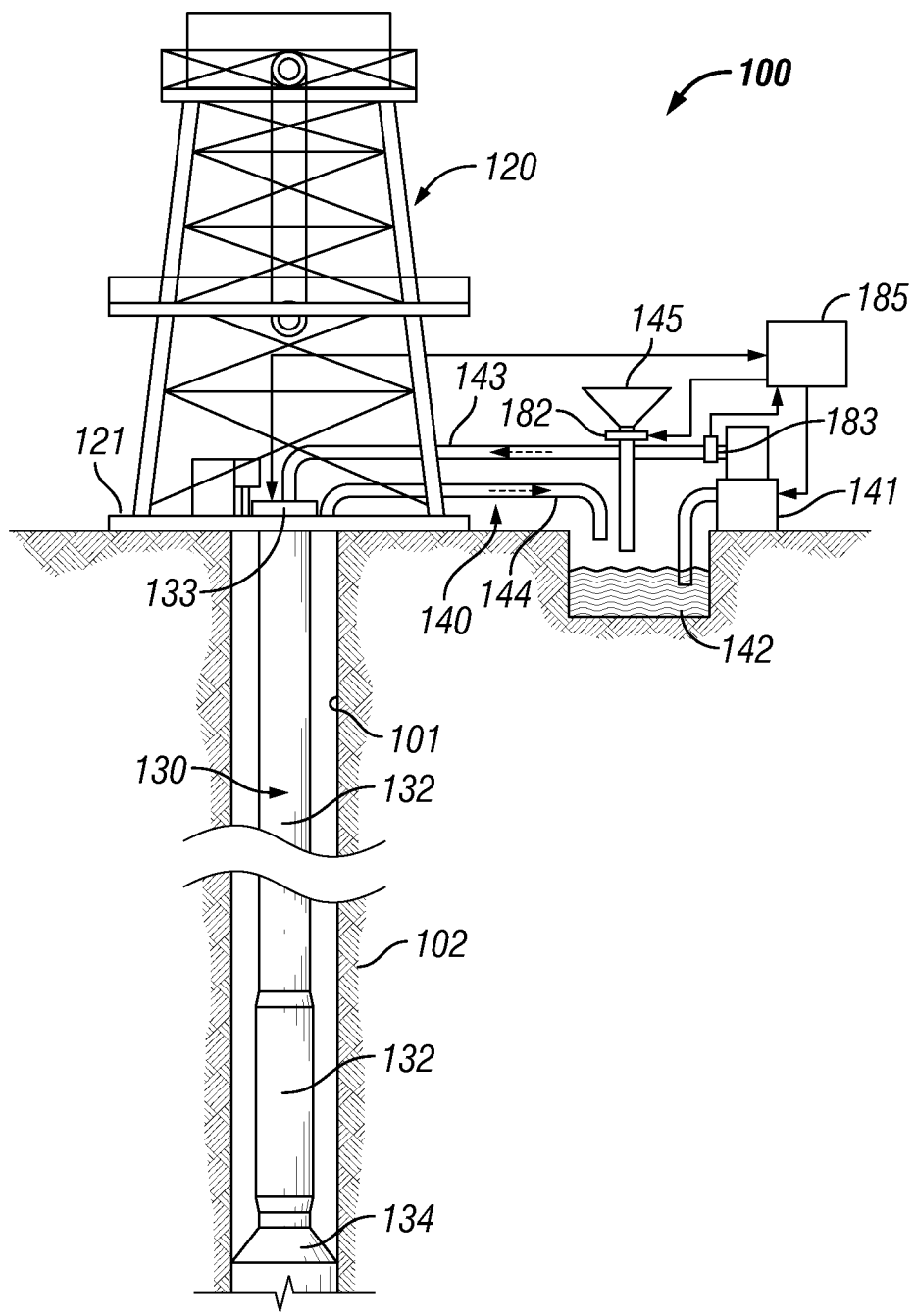
FIG. 4 illustrates a simplfied process diagram of a drill site according to one or more embodiments disclosed herein.

Referring now to FIG. 3, a fracturing site is shown. At the fracturing site 200, a fracturing fluid or slurry is pumped from a surface 118 of a well 120 to a wellbore 122 during a fracturing operation. The fracturing site 200 includes a plurality of water tanks 221, which feed water to a gel maker 223. The gel maker 223 combines water from the tanks 221 with a gelling agent to form a gel. The gel is then optionally sent to a blender 225 where it is mixed with a proppant from a proppant feeder 227 to form a fracturing fluid. The gelling agent increases the viscosity of the fracturing fluid and allows the proppant to be suspended in the fracturing fluid. It may also act as a friction reducing agent to allow higher pump rates with less frictional pressure.

The fracturing fluid is then pumped at low pressure from the blender to a plurality of plunger pumps 201 as shown by solid lines 212. Each plunger pump 201 receives the fracturing fluid at a low pressure and discharges it to a common manifold 210 at a high pressure as shown by dashed lines 214. The manifold 210 then directs the fracturing fluid to the wellbore 122 as shown by solid line 215. As shown, a computerized control system 229 may be employed to direct the entire fracturing site 200 for the duration of the fracturing operation. In one or more embodiments, the in-line viscometer of the present disclosure may be incorporated into a fluid flow line downstream of the gel maker 223, which may include before or after blender 225.

In some embodiments, the presently disclosed system may be independent units which are plumbed to a process trailer (such as those containing gel maker 223, blender 225, plunger pumps 201) which may be deployed to a site for each oilfield operation in which they are used. A particular viscosity measurement system may be connected differently to the process trailer for different jobs. The viscosity measurement system may be provided in the form of an equipment package mounted to a standard trailer for ease of transportation by a tractor.

As shown in FIG. 3, a drilling site 100 is provided for drilling a wellbore into an earthen formation 102 to exploit natural resources such as oil. The drilling system 110 includes a derrick 120, a drill string assembly 130, a fluid circulation system 140, and a control unit 185. The derrick 120 is built on a derrick floor 121 placed on the ground. The derrick 120 supports the drill string assembly 130 which is inserted into a wellbore 101 and carries out a drilling operation.

The drill string assembly 130 includes a drill string 131, a bottom hole assembly 132, and a drive system 133. During an operation for drilling the wellbore 101, the drill pipe 131 is rotated by the drive system 133, and this rotation is transmitted through the bottom hole assembly 132 to the drill bit 134.

The fluid circulation system 140 includes a fluid pump 141, a mud pit 142, a supply line 143, and a return line 144. The fluid circulation system 140 circulates a wellbore fluid through the drill string assembly 130 and into the wellbore 101. Specifically, the fluid pump 141 pumps wellbore fluid, which is reserved in the mud pit 142, through the supply line 143, and then, the wellbore fluid is injected into the drill string 131. The wellbore fluid injected into drill string 131 is then discharged from the drill bit 134 to the bottom of the wellbore 101 and returns to the mud pit 142 through the return line 144.

When drilling a wellbore 101, fluids that exit drill bit 134 and circulate through the wellbore 101 may form a thin, low-permeability filtercake to seal permeable formations 102 penetrated by the bit 134. These well fluids may consist of synthetic polymers or biopolymers (such as to increase the rheological properties (e.g. plastic viscosity, yield point value, gel strength) of the drilling mud), clays, polymeric thinners, flocculants, and organic colloids added thereto to obtain the required viscosity and filtration properties. Heavy minerals, such as barite or carbonate, may also be added to increase density. Such additives are added to the fluid via feed hopper 145 and may be metered by metering valve 182. While feed hopper 145 is shown as adding additives directly into mud pit 142, it is envisioned that one or more mixers, tanks, etc. may be used for the formulation and mixing of the fluid.

The control unit 85 monitors properties and conditions of the fluids in the wellbore 101 and the fluid circulation system 140, including the viscosity of the fluid measured inline in accordance with the present disclosure. The control unit 185 includes, for example, a central processing unit (CPU), a read only memory (ROM), a random access memory (RAM), input/output ports, memory, and the like. The control unit 185 is electrically connected to the drive system 133, fluid pump 141, choke valve 183, metering valve 182, as well as in-line viscometer (not shown), which may reside within supply line 143 or between mud pit 142 and pump 141. Upon measurement of the in-line fluid viscosity, the control unit may adjust one or more of metering valve 182, choke valve 183, pump 141, or a mixer (not shown).

In order to ensure that the presently described in-line viscometer process produces usable, valid results, the in-line measurements may be correlated to a base line laboratory device. Any deviation may be calculated, and the appropriate corrections to the process may be performed. Such corrections may include additive addition rate or base fluid addition rate changes. The fluid may be measured, monitored, and controlled by its viscosity at a specified shear rate and temperature. For example, the shear rate may be specified to be in the range of between 150-600 $s^{-1}$ and the temperature may be in the range of between 40-120° F. Furthermore, in may no longer be necessary to characterize the non-Newtonian fluid across multiple shear rates such as, for example, using the VISCOLINE rheometer (manufactured by Krohne, Inc). The presently described process simply allows for process control based on the feedback signal at a predetermined shear rate and temperature.

For the correlation to a base line laboratory device, a Fann35 viscometer may be used for the correlated meter. For example, one may run a control test fluid, through the above described process, with a known Fann35 curve of viscosity as function of shear at a fixed temperature. The control test fluid may be fed through the process at different flow rates in a fixed sampling loop. A measurement of the viscosity is taken using the above described process, and the measurement is correlated and/or compared the viscosity curve of the Fann35 for the control test fluid and the process slurry. Any discrepancies in the measurements may then be calculated and factored in to the process control loop.

Figure 5:
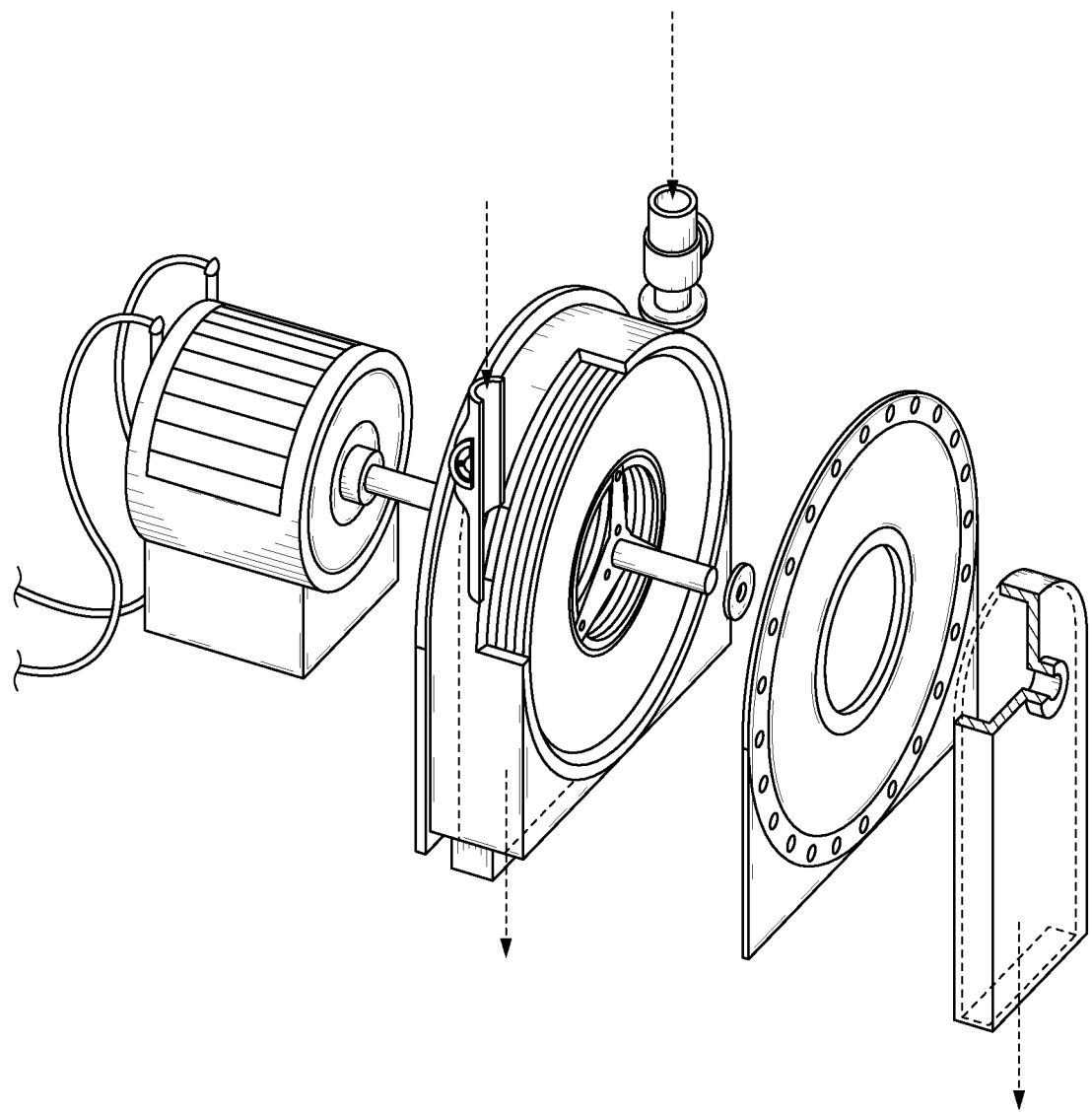
FIG. 5 illustrates a tesla turbine type viscosity measurement device according to one or more embodiments disclosed herein.

Any suitable viscometer may be employed to enable the above described in-line process for rheological characterization and process control. For instance, examples of such a device may include a Tesla Turbine, illustrated in FIG. 5. For this type of in-line viscosity measurement device, a fluid flow rate is set by a positive displacement pump. The slurry is pumped into the inlet of the turbine and power is generated within the turbine. The power and RPM, which corresponds to shear rate of the slurry, of the turbine can then be correlated to the flow rate and viscosity of a known Fann35 curve for the slurry as described above. The Tesla Turbine can be made small enough to fit on existing trailers and has a high, repeatable accuracy. If desired, two or more Tesla Turbines may be installed in series to get an average viscosity across multiple pressure drops.

Figure 6A:
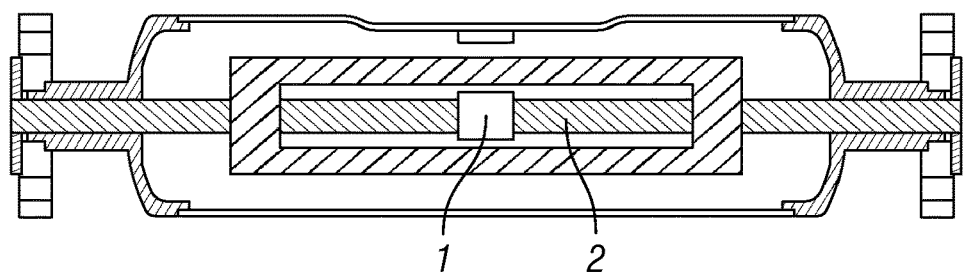
FIGS. 6A, 6B, and 6C illustrate a coriolis flowmeter type viscosity measurement device according to one or more embodiments disclosed herein.
Figure 6B:
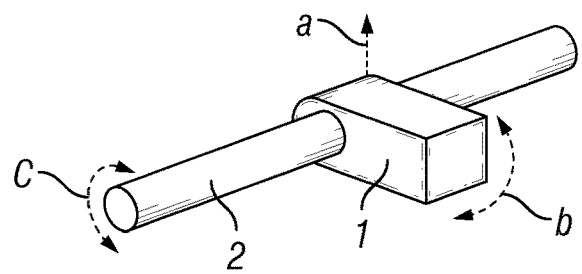
Figure 6C:
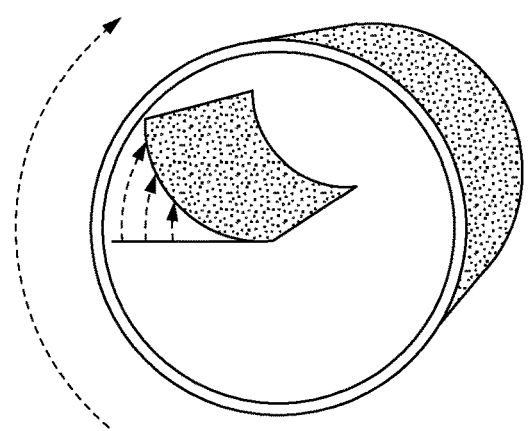

Another such in-line viscosity measurement device may be a Coriolis flowmeter, illustrated in FIG. 6A. Coriolis flowmeters, such as the Promass Coriolis flowmeter manufactured by Endress+Hauser, use the torsional movement of a single straight measuring tube 2 and pendulum 1 to measure the viscosity of the fluid. As illustrated in FIG. 6B, the translator movement (a) of the measuring tube 2, used to measure density and mass flow of the fluid, and torsional movement (c) of the measuring tube, and the torsional movement (b) of pendulum 1 are used to calculate viscosity. FIG. 6C illustrates how the shear rate of the fluid effects the torsional movement of the measuring tube. This measurement method may provide accurate and repeatable results for Newtonian fluids. For non-Newtonian fluids, viscosity calculations are repeatable but accuracy is adversely affected by shear rates variations. These accuracy variations may be characterized by comparison to a known Fann35 curve and then the process control may be adjusted accordingly as described above.

Using a Coriolis flowmeter, the viscosity may also be measured accurately in one of various ways. For example, in one or more embodiments, momentarily (e.g., from about 2 to about 60 seconds) reducing flow rate of the non-Newtonian fluid to zero may remove shear induced by the movement of fluid parallel to the axis of the measuring tube. Such a technique could also be referred to as pulsing. "Pulsing" the non-Newtonian fluid could therefore allow for process control by repeating viscosity measurements at given time intervals, allowing for a new sample of the measured fluid. Another way of stopping the flow within the measuring inner tube would be to divert the flow to a parallel channel while taking the viscosity measurement on the inner tube. This would allow for uninterrupted liquid delivery while keeping the viscosity measurement capabilities.

In one or more other embodiments, altering the torsional oscillation frequency (from about 1 Hz to about 10,000 Hz) could change the shear rate of the fluid and therefore allow for calculations of the viscosity at different shear rates. Altering the frequency may be done by changing the frequency of the excitation mechanism which may be electronically controlled. This may be done by changing the frequency of the current input that allows for oscillation of the magnetic field used to vibrate the tube. Measuring the viscosity of non-Newtonian fluids at various frequencies could allow for the full rheological characterization of the fluid. As used herein, the term "full rheological characterization" means that enough data points are obtained to establish the relationship that relates viscosity to shear rate. In the case of a power law fluid, 2 data points are enough (i.e., at two different frequencies), but a greater number of data points allow for a better characterization of the fluid by improving the fitting of the data points to theoretical behavior.

In one or more other embodiments, torsional oscillation may create shear rate variations in the cross section of the tube, creating noise in the viscosity calculations. However, rotating the straight-tube measuring tube around its longitudinal axis could reduce shear rate variations. Such a procedure may need to be performed (1) at zero flow or (2) with a pendulum attached to the measuring tube that balances the forces and allows for simultaneous mass flow measurements. This method could implement a controlled-stress technique.

Any suitable device may be employed to enable the above described process control. For instance, example specifications of such a device may include a device with the functionality able to provide a continuous point measurement (viscosity at predetermined shear rate from 1 $s^{-1}$ to 1000 $s^{-1}$, such as, for example, 171 $s^{-1}$, at room temperature (25° C.)) for a process fluid (which maybe a Newtonian or non-Newtonian fluid). Accuracy may be measured against predetermined viscosity measurements taken by Fann35 viscometer (bench top viscometer). The in-line viscometer should have an accuracy of at least within about 4%, such as for example, from about 1% to about 4% of the Fann35 viscometer measurements. Additionally, the device should be as compact as possible for integration into surface equipment, the device should be robust for field applications but need not be explosion proof, and the device should provide viscosity data by means of analog (4-20 mA signal) and/or digital signals.

Figure 7:
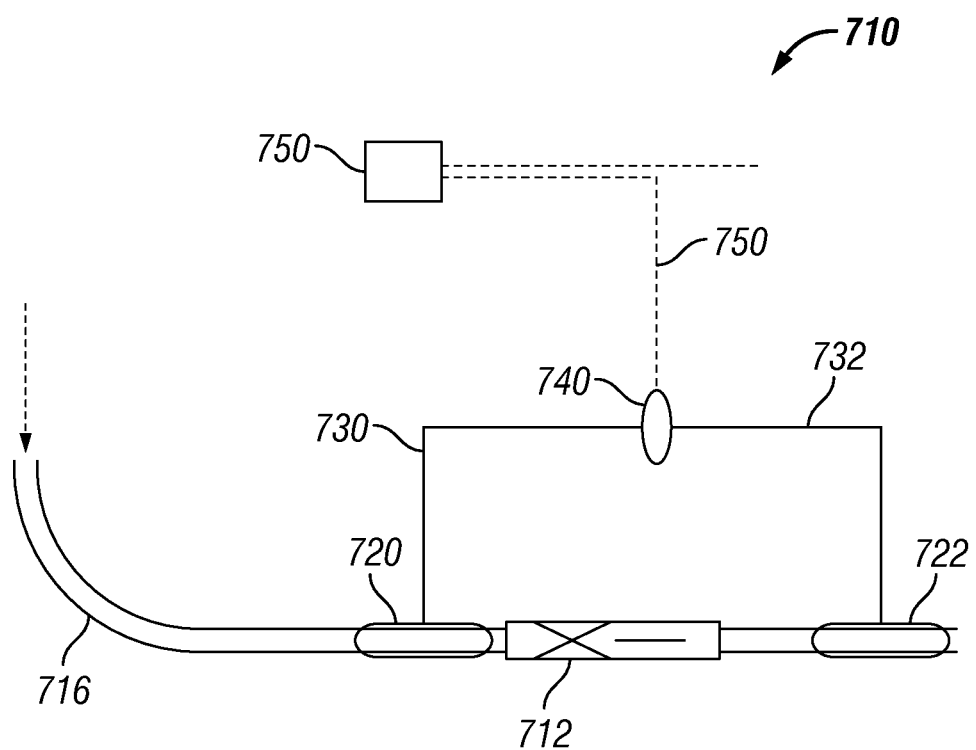
FIG. 7 illustrates a simplified process diagram according to one or more embodiments disclosed herein.

Referring now to FIG. 7, an embodiment of an apparatus for the in-line measurement of viscosity is shown. As shown, the apparatus 710 comprises a static mixer 712. All the fluid coming from a main supply pipe 716 is passed therein and immediately returns into the main pipe 716 afterwards. However, one could also deviate only a portion of the fluid through the apparatus 710 from the main pipe 716 or simply draw fluid from a tank (not shown) for analysis. The fluid in main pipe 716 may be an effluent from a mixer (not shown) where an additive and a base fluid from an additive supply feeder and a base fluid supply, respectively, are mixed (not shown).

Most static mixers can be classified in either one of two categories. The first category includes the ones in which the mixing occurs by rotation in a tube. These static mixers are relatively long and the pressure drop therein is low. The second class comprises the static mixers in which the mixing occurs by stretching the fluid. These mixers are short and the pressure drop therein is high. Either type may be used, but may be of the first type (mixing occurs by rotation in a tube) in particular embodiments. The static mixer may have geometric contrainsts $K_s$ and $K_p$ specific to the mixer, which depend on the geometry of the static mixer and may be obtained through a prior calibration procedure from a power correlation between a Newtonian model fluid and a non-Newtonian power law fluid. Such calibration may be described in U.S. Pat. No. 6,412,337.

The pressure drops through the static mixer 712 is expressed as a pressure differential using appropriate sensors or any other suitable means. The first cell 720 is mounted on the apparatus 710 upstream of the inlet of the static mixer 712 and, the second cell 722 is mounted downstream of the outlet of the static mixer 712. These cells 720, 722 are connected as a pair by means of a circuit of rigid tubes 730, 732 leading to a differential pressure transducer 740. The first cell 720 is connected to a first side of the differential pressure transducer 740 by means of the first tube 730. The second cell 722 is connected to a second side of the differential pressure transducer 740 by means of the second tube 732.

The tubes 730, 732 are filled with a substantially incompressible liquid, such as water or ethylene glycol. Each cell 720, 722 comprises a deformable membrane (not shown made of material that is able to correctly transmit the pressure to the incompressible liquid and resist the abrasion of the fluid, such as natural or synthetic rubber.

The pressure drop of the fluid through the static mixer 712 is measured by the differential pressure transducer 740, which includes an output terminal 750 by which a corresponding differential pressure signal ΔP is sent via wires 752. Output terminal 750 then characterizes the shear of the fluid and may also calculate the apparent viscosity, discussed in greater detail below. After the fluid has been shear and rheologically characterized, the fluid may recycled to the mixer upstream of static mixer 712, fed to a pump to be pumped downhole in a wellbore, or both.

The fluid being tested flows at a mean flow velocity (V) in a pipe having a given diameter (D). The mean flow velocity (V) is expressed in terms of meters per second or the equivalent. The values of the mean flow velocity (V) and the diameter (D) are preferably those of the main pipe on which is installed an apparatus according to the present embodiment. The diameter (D) should remain constant throughout the path of the fluid in the apparatus in order to minimize the perturbations that might be generated in the fluid.

There are two main ways of determining the mean flow velocity (V). The first is to measure the mean flow velocity (V) with an appropriate sensor. The second is to calibrate the supply pump used to move the fluid. The supply pump is either the supply pump of the system to which the rheological apparatus is connected or either an additional pump provided therewith.

When a fluid flows in a pipe, the effective shear rate (γ) is linked to the mean flow velocity (V) of the fluid by:

$$\gamma = K_s \frac{V}{D}$$

where D is the diameter of the pipe and $K_S$ is a constant that depends on the geometry of the mixer, discussed above. Power law fluids are characterized by the following relation:

$$\tau = K\gamma^n$$

where τ represents the stress, k is the consistency index, and n is the power law index.

U.S. Pat. No. 6,412,337 relates to an apparatus and method for measuring the rheological properties of a power law fluid, requiring the need for two static mixers and a pressure drop measurement across them. Specifically, U.S. Pat. No. 6,412,337 calculates k and n for the power law fluids according to the following equations:

$$n = 1 + \frac{\log\left[\frac{\Delta P_2 K_{p1} L_1}{\Delta P_1 K_{p2} L_2}\right]}{\log\left[\frac{K_{s2}}{K_{s1}}\right]}$$

$$k = \frac{\Delta P_1 D^{(n+1)}}{K_{p1}[8K_{s1}]^{(n-1)} V^n L_1}$$

Thus, such equations use a $\Delta P_1$ and a $\Delta P_2$. The equation for n only requires a ratio of $\Delta P_2/\Delta P_1$ and k requires at least one ΔP measurement. Disclosed herein is a process to empirically denote the ratio of differential pressures as a constant for a given flow rate and a given set of fluids. By doing this, it may be possible to achieve the desired rheological characterization with only a single static mixer.

Apparent viscosity (η) can be calculated for a power law fluid with the following equation, using the:

$$\eta = k\left(K_s' \frac{V}{D}\right)^{n-1}$$

where $K_S'$ is the geometrical constant of a given location where the apparent viscosity is to be measured. For instance, if the apparent viscosity (η) has to be calculated in the static mixer, the value of $K_S'$ is that of $K_S$. If the apparent viscosity (η) has to be calculated in a free pipe, the value of $K_S'$ is 8, which is a value known in the art.

Figure 8:
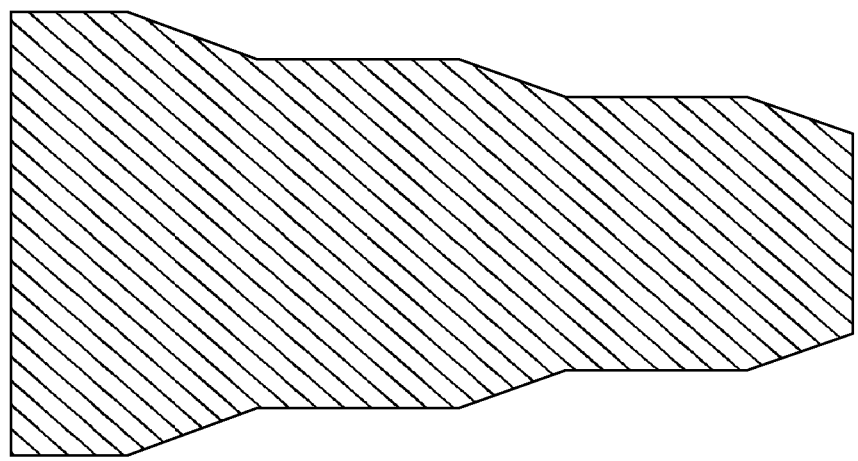
FIG. 8 illustrates a cascade nozzle according to one or more embodiments disclosed herein.

In such a process, in order to avoid buildup of fluid, a larger static mixer may be used. In one or more other embodiments, use other shear characterization devices other than static mixer may also be used. For example, illustrated in FIG. 8 is an example of on such alternate device; a cascading nozzle. This type of nozzle creates a differential pressure along the length of the nozzle that may be used to characterize the rheological properties as described above. In some embodiments, an orifice or venturi may also be used for the same purpose.

While the present teachings have been illustrated with respect to one or more embodiments, alterations and/or modifications may be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:

1. A method for viscosity measurement of non-Newtonian fluid for in-line measurement and process control comprising:
    adding one or more additives to a base fluid at a mixer to form the non-Newtonian fluid;
    feeding the entirety of the non-Newtonian fluid to an in-line viscosity measurement device;
    measuring the viscosity of the non-Newtonian fluid to obtain a rheological measurement and a measured effluent;
    adjusting the addition of the one or more additives to the base fluid, in real-time, based on the rheological measurement;
    feeding at least a portion of the measured effluent to a pump; and
    pumping the measured effluent to one or more downstream systems.

2. The method of claim 1, further comprising recycling a second portion of the measured effluent to the mixer to dilute the measured effluent.

3. The method of claim 1, wherein the adjustment of the additive is either an increase or decrease in the amount of additive being added to the base fluid.

4. The method of claim 1, further comprising feeding the base fluid to the mixer from a base fluid source or supply tank.

5. The method of claim 1, wherein the base fluid is fed to the mixer at a selected rate.

6. The method of claim 1, wherein the non-Newtonian fluid is shear-thinning.

7. The method of claim 1, wherein the viscosity of the non-Newtonian fluid is in the range of between 1-10,000 cP.

8. The method of claim 1, wherein a shear rate in the viscosity measurement device is maintained at a rate of 150-600 $s^{-1}$.

9. The method of claim 1, wherein a temperature of the fluid in the viscosity measurement device is maintained in a range of 40-120° F.

10. The method of claim 1, wherein feeding comprises feeding the entirety of the non-Newtonian fluid directly to the in-line viscosity measurement device.

11. A system used to prepare a slurry comprising an additive and a base fluid, the system comprising:
    a base fluid supply;
    an additive supply feeder;
    a mixer that blends additive supplied by the additive supply unit and base fluid supplied by the base fluid supply to form a slurry;
    an in-line viscosity measurement device for measuring the viscosity of the slurry during operation of the system by measuring a pressure differential created across a shear characterization device of the in-line viscosity measurement device;
    a control system configured to adjust a rate of the additive addition, during operation of the system, in response to the measured viscosity of the slurry; and
    a pump for pumping the measured slurry to downstream systems, wherein the in-line viscosity measurement device is located intermediate the mixer and the pump.

12. The system of claim 11, wherein at least a portion of the slurry exiting the in-line viscosity measurement device is recycled to the mixer.

13. The system of claim 11, wherein the viscosity of the slurry is in the range of between 1-10,000 cP.

14. The method of claim 11, wherein the shear rate in the viscosity measurement device is maintained at a rate of 150-600 $s^{-1}$.

15. The method of claim 11, wherein a temperature of the fluid in the viscosity measurement device is maintained in the range of 40-120° F.

16. The system of claim 11, wherein the slurry is a non-Newtonian fluid.

17. The system of claim 16, wherein the slurry is shear thinning.

18. The system of claim 11, wherein the residence time of the mixer is sufficient to allow for an adjustment of the viscosity of the slurry based on the measurement obtained from the in-line viscosity measurement device.

19. The system of claim 18, wherein the adjustment of the viscosity of the slurry is based on at least a performance curve generated by the control system.

20. An apparatus used to prepare and characterize a wellbore fluid, the apparatus comprising:
    a base fluid supply unit configured for supplying a base fluid;
    an additive supply feeder configured for supplying an additive;
    a mixer configured for mixing the additive and the base fluid and forming a wellbore fluid;
    a pump configured for pumping the wellbore fluid to a location down the wellbore; and
    an in-line viscosity measurement apparatus configured for measuring the viscosity of the wellbore fluid during operation of the apparatus, the in-line viscosity measurement apparatus being located intermediate the mixer and the pump, the in-line viscosity measurement apparatus comprising:

a shear characterization device configured for creating a pressure differential upstream and downstream of the shear characterization device; and
a plurality of pressure transducers configured for measuring the pressure differential of the shear characterization device.

* * * * *